United States Patent [19]

Kirsch et al.

[11] Patent Number: 4,733,664
[45] Date of Patent: Mar. 29, 1988

[54] SURGICAL CLIP, APPLIER, AND METHOD

[75] Inventors: Wolff M. Kirsch, Albuquerque, N. Mex.; Zhu Y. Hua, Shanghai, China; Robert B. Cushman, Cedar Crest, N. Mex.

[73] Assignee: University of New Mexico, Albuquerque, N. Mex.

[21] Appl. No.: 787,101

[22] Filed: Oct. 15, 1985

Related U.S. Application Data

[63] Continuation-in-part of Ser. No. 556,917, Dec. 1, 1983, Pat. No. 4,586,503.

[51] Int. Cl.$^4$ .............................................. A61B 17/04
[52] U.S. Cl. ............................... 128/334 R; 128/321; 128/326; 227/DIG. 1
[58] Field of Search .................... 227/19, 1 R, 15, 83, 227/DIG. 1; 294/86.1, 86.27, 86.29, 86.3, 86.31, 86.32, 86.33; 411/2, 39–43, 475, 476, 904, 920; 128/325, 321, 354 R, 334 R, 336, 337, 346, 326

[56] References Cited

U.S. PATENT DOCUMENTS

| | | | |
|---|---|---|---|
| 984,629 | 2/1911 | Wheeler | 411/920 |
| 2,501,567 | 3/1951 | Huck | 411/39 |
| 2,635,501 | 4/1953 | Eichner | 411/39 |
| 2,662,524 | 12/1953 | Hudgins . | |
| 3,192,821 | 7/1965 | Siebol | 411/41 |
| 3,232,089 | 1/1966 | Samuels et al. . | |
| 3,361,133 | 1/1968 | Kimberly et al. . | |
| 3,446,212 | 5/1969 | Le Roy . | |
| 3,604,425 | 9/1971 | Le Roy . | |
| 3,774,438 | 11/1973 | Weston | 227/DIG. 1 R |
| 3,807,406 | 4/1974 | Rafferty et al. . | |
| 3,827,277 | 8/1974 | Weston | 227/DIG. 1 R |
| 3,856,017 | 12/1974 | Perisse et al. . | |
| 3,906,957 | 9/1975 | Weston | 227/DIG. 1 R |
| 3,916,909 | 11/1975 | Kletschka et al. . | |
| 3,958,576 | 5/1976 | Komiya | 227/DIG. 1 C |
| 3,980,086 | 9/1976 | Kletschka et al. . | |
| 4,004,835 | 1/1977 | Taylor | 294/86.33 |
| 4,038,987 | 8/1977 | Komiya | 128/321 |
| 4,049,002 | 9/1977 | Kletschka et al. . | |
| 4,096,864 | 6/1978 | Kletschka et al. . | |
| 4,324,248 | 4/1982 | Perlin . | |
| 4,350,160 | 9/1982 | Kolesov et al. . | |
| 4,394,864 | 7/1983 | Sandhaus | 128/321 |
| 4,396,139 | 8/1983 | Hall et al. | 227/19 |
| 4,397,312 | 8/1983 | Molko . | |
| 4,453,756 | 6/1984 | Haag | 294/86.29 |

OTHER PUBLICATIONS

"The Technical Aspects of the Vascular Stapler", R. F. Mallina, *Division of Instrumentation*, Jan. 8, 1963, pp. 353–364.
"Surgical Stapling", R. F. Mallina et al, pp. 48–56.
"The Problem of Small Vessel Anastomosis", I. J. Vogelfanger, et al, Dept. of Anatomy, Ottawa University, and the National Research Council of Canada, Div. of Mechanical Engineering, Aug. 1962, pp. 354–362.
"Microvascular Stapling", I. J. Vogelfanger et al, Ottawa pp. 39–50.
"A New Type of Vessel-Suturing Apparatus", K. Inokuchi, Fukuoka, Japan, *A.M.A. Archives of Surgery*, vol. 77, Dec., pp. 954–957.
"Experimental Anastomosis of the Left Internal Mammary . . . ", S. E. Carroll, Canadian Journal of Surgery, Oct. 1964, pp. 468–469.
"A Simple New Apparatus for Small Vessel Anastomosis (Free Autograft of the Sigmoid Included)", Nakayama et al, *Surgery*, Dec. 1962, pp. 018-931.

(List continued on next page.)

*Primary Examiner*—Gene Mancene
*Assistant Examiner*—J. Hakomaki
*Attorney, Agent, or Firm*—Charles W. Fallow; Martin P. Hoffman; Mitchell B. Wasson

[57] ABSTRACT

A surgical clip is disclosed having a pair of spaced arms joined by a bridge that is deformed by pulling on a tang, which is connected to the bridge by a frangible neck. Also disclosed is a tool for pulling the tang, and an anastomosis procedure that may be quickly performed using the clip and tool.

10 Claims, 7 Drawing Figures

OTHER PUBLICATIONS

"The Effect of Dextran on the Incidence of Thrombosis in Microvenous Nakayama Ring Pin Anastomoses", Wiman et al, *Scand J. Plast Reconstr Surg* 13 pp. 263–268.

"Aorto-Pulmonary Shunt in the Premature Infant", Roe, *The Journal of Thoracic and Cardiovascular Surgery*, pp. 437 & 438.

"A New Gearing Approximator for Microsurgical Vascular Anastomoses", E. Wintermantel, Acta Neurochirurgica 50, 237–242 (1979).

"Anastomosis of Small Veins with Suture or Nakayama's Apparatus", Ostrup, *Scand J. Plast Reconstr Surg* 10; 9–17, 1976.

"The Russian Stapler in Small Artery Anastomoses and Grafts", Williams et al, pp. 170–172.

"Stapler for A-V Anastomosis: Simplified, Immediate Vascular Access, Ivanovich et al, vol. XXIII *Trans. Am. Soc. Artif. Intern. Organs*, 1977, pp. 716–718.

"Suture Anastomosis of Small Arteries", Chase et al, *Surgery, Gynecology & Obstetrics*, Jul. 1963, pp. 44–46.

"Thrombogenesis in Experimental Microvascular Anstomosis", Shimizu et al. *Journal of Microsurgery*, Jul. Aug. 1979, pp. 39–49.

"A Technique of Small Artery Anastomosis", Chase et al, *Surgery, Gynecology & Obstetrics*, Mar. 1963, pp. 381–386.

"A Simple Method for Closure of the Potts Anastomosis with a Mechanical Stapler", Leand et al., *The Journal of Thoracic and Cardiovascular Surgery*, vol. 42, No. 2, Aug. 1971, pp. 285–289.

"Small Vessel Anastomosis", John Cobbett, *British Journal of Plastic Surgery*, pp. 16–20.

"A New Simple Apparatus for Anastomosis of Small Vessels", Nakayama et al. *Journal of the International College of Surgeons*, vol. 38, No. 1, Jul. 1962, pp. 12–26.

"Internal Mammary-Coronary Artery Anastomosis", Goetz et al, *J. Thoracic and Cardiovas. Surg.*, vol. 41, No. 3, Mar. 1961, pp. 378–386.

"A Concept of Automation in Vascular Surgery: A Preliminary Report on a Mechanical Instrument for Arterial Anastomosis", Vogelflanger et al, *Canadian Journal of Surgery*, vol. 1, Apr. 1958, pp. 262–265.

"Stapling Device for End-to-Side Anastomosis of Blood Vessel", K. Inokuchi, M. D., Archives of Surgery, vol. 82, Mar., 1961, pp. 337–341.

"A New Method for Anastomosing Blood Vessels by Manually Applied Clips", Gonzalez et al, pp. 178–181.

"Vascular Anastomosis-Sutures, Staples or Glue?", Zingg et al, *Canad. Med. Ass. J.*, Oct. 10, 1964, vol. 91, pp. 791–794.

"Repair of Small Arteries with Contact Cement and Teflon Graft", Khodadad et al, pp. 552–560.

"New Method of Surgical Treatment of Blood Vessel Lesions", P. I. Androsov, *A.M.A. Archives of Surgery*, pp. 902–910.

"A Non-Suture Small Vessels Prosthetic Connector", Selker et al, pp. 50–52.

Samuels, "Method of Blood Vessel Anastomosis . . . ", A.M.A. Archives of Surgery, pp. 29–38.

Samuels, "The Use of Metal Clips in the Surgery of Blood Vessels", Bulletin de la Societe International de Chirurgie, No. 1, 1962, pp. 21–33.

Samuels et al, "Technique of Closure of Skin Incisions . . . ", Surgery, vol. 59, No. 5, May 1966, pp. 741–743.

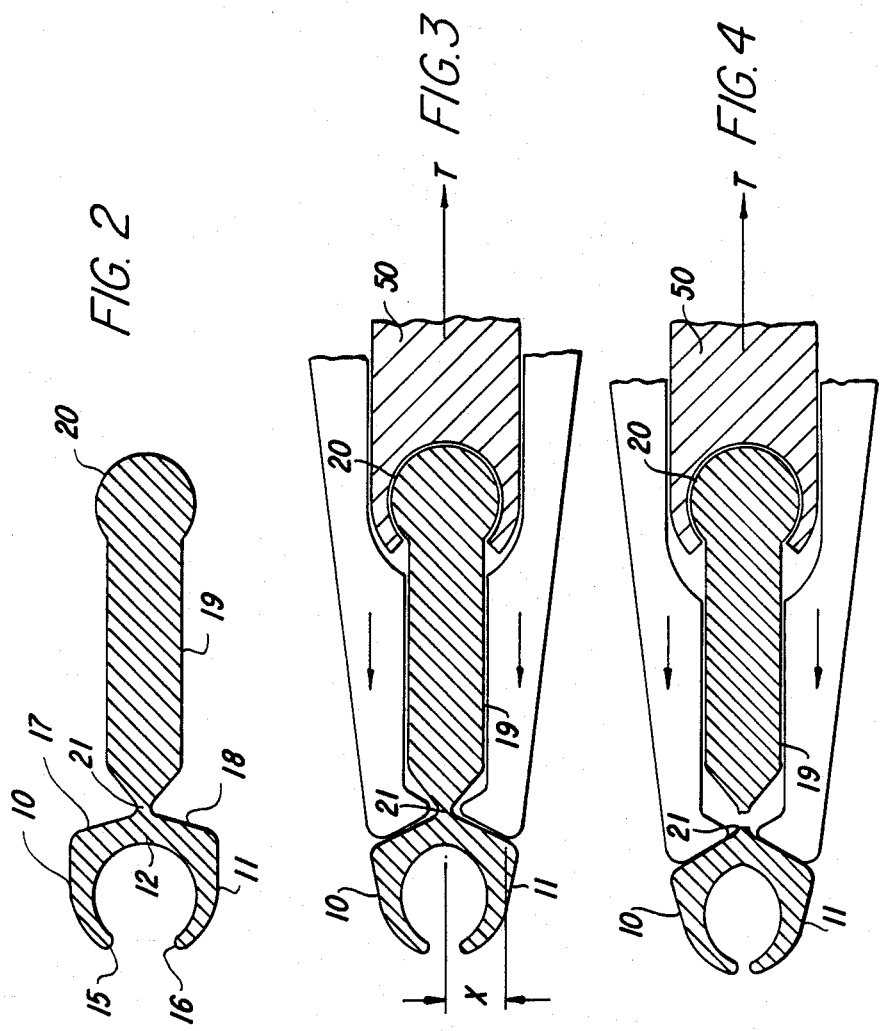

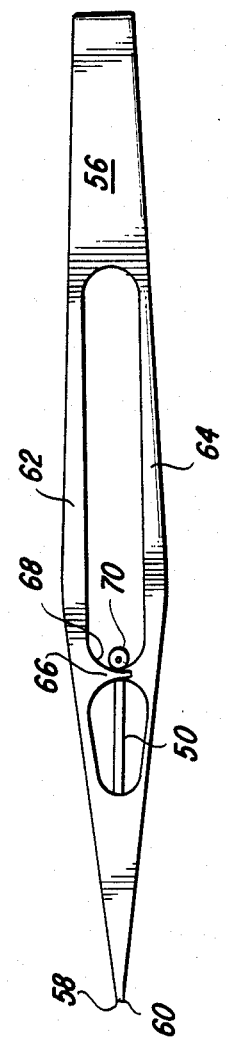

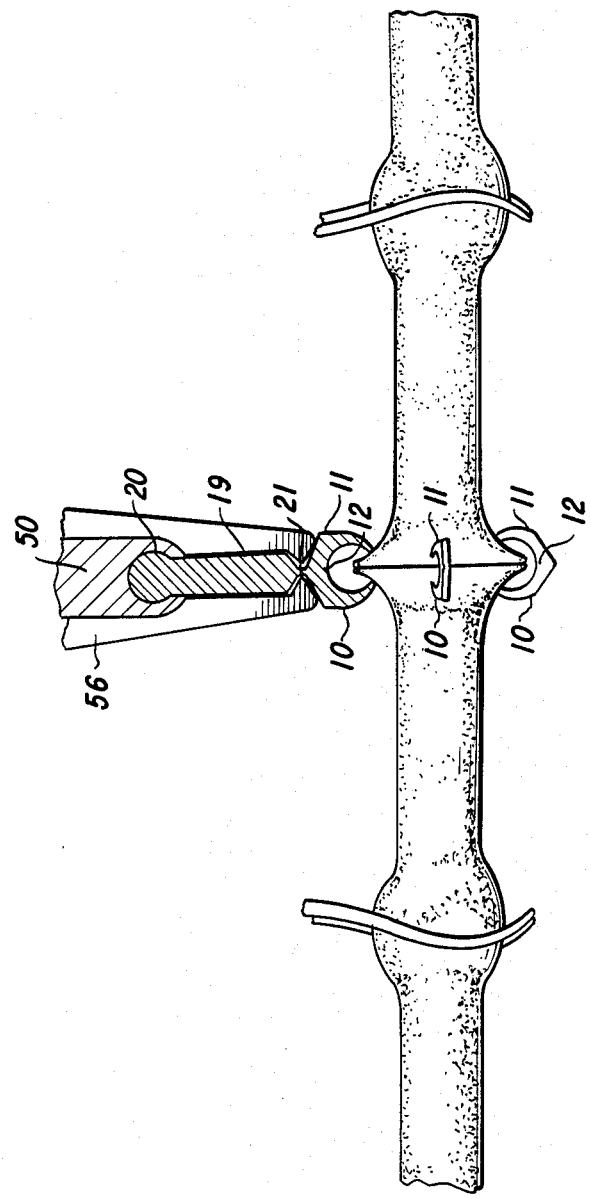

SURGICAL CLIP, APPLIER, AND METHOD

This application is a continuation-in-part of copending application Ser. No. 556,917, filed Dec. 1, 1983, now U.S. Pat No. 4,586,503.

BACKGROUND OF THE INVENTION

This invention relates generally to the field of surgery, and more particularly to the field of vascular microsurgery.

In various surgical procedures, it is necessary to unite or reunite very small blood vessels, nerves and the like. The procedure of joining blood vessels is known as vascular anastomosis. Particularly in neurosurgical procedures and in the reattachment of severed body members, the number of anastomoses required can be very numerous, and accordingly, it is advantageous and frequently necessary to perform each such connection quickly yet properly.

A conventional end-to-end anastomosis is illustrated in FIG. 1, which shows a pair of vessels 1 and 2, each held by a respective clamp 3 or 4 while it is sutured around its circumference. The vessel ends are first approximated by inward traction on the two vascular clamps. The vessels may then be preliminarily interconnected by placing sutures at two, three or four spaced locations around the circumference of the vessel—note the threads 5 and 6 in tension—whereafter the suturing 7 is completed with a needle 8. Various suturing techniques are known, all of which are designed to: (a) provide a leak-proof connection; (b) provide adequate tensile strength; (c) avoid unnecessary restriction of the vessel; (d) avoid unnecessary tearing and other trauma to the vessel; and (e) promote rapid and thorough healing. Some of these objectives become increasingly difficult to satisfy as smaller and smaller anastomoses are carried out; furthermore, the danger of accidentally catching the rear or distal wall of the vessel with the needle as the proximal wall is being sutured increases with diminishing vessel size.

With all vascular suturing techniques, thrombosis or clotting tends to occur at the points of needle penetration. While this clotting would not usually be sufficient to occlude larger vessels, in smaller veins and arteries a significant constriction or complete occlusion of the vessel can result from clotting. The problem has been summarized thus: "It is apparent to us that the damage to vascular endothelium caused by the microvascular needle perforation is considerable. The amount of subsequent platelet aggregation and clot formation can be extensive, and these platelets are known to release vasoactive substances that can alter vessel diameter. This could diminish blood flow through a 1- to 2-mm vascular anastomosis expected to give immediate increased flow to an underperfused region of the brain." D. Pagnanelli et al, *The Cutting Edge Microsurgical Needle*, Journal of Neurosurgery, volume 59, no. 3, pages 510–512 (Sept. 1983).

In addition to the physiological damage done by suturing, it is also significant that suturing, particularly of small vessels, is a very tedious time-consuming procedure which can preoccupy and fatigue a surgeon over the course of a long procedure. A more rapid way of performing microvascular anastomoses could free the surgeon for other tasks, and could shorten surgical procedures as well. The need for a workable, rapid, non-suturing technique for microsurgery is obvious.

Various non-suture devices and techniques for performing anastomoses are known, particularly for intestinal and colorectal anastomoses, for which various stapling apparatus and methods have been known for some years. Known stapling techniques, however, require penetration of the organ wall, and if applied to vascular anastomoses, the problems of clotting and the like, as described above, could be expected to arise. For vascular anastomosis, various other non-suture mechanical clamps have been suggested. Such clamps frequently include a permanent or sacrificial ferrule or the like and means for clamping the vessel against the ferrule so that penetration of the vessel wall is avoided. However, clamps of this type have not gained widespread acceptance.

In view of the foregoing, this invention has been made with a view to substantially increasing the speed of microvascular anastomoses and other procedures while avoiding the clotting problems caused by conventional suturing procedures. Another object is to reduce the material costs and duration of microsurgical procedures.

A further object of the invention is to provide a permanently implantable surgical clip for use in place of microvascular suturing. Yet another object is to provide the surgeon with a clip that can be easily held and applied during vascular anastomoses.

This invention relates generally to a surgical procedure such as an anastomosis wherein a pair of tissues is approximated, then partially everted, and then joined by placing the arms of a surgical clip over the adjoined tissues and crimping the arms about the tissues in such a way as to hold the tissues together without penetrating them.

The invention is also directed to a vascular surgical clip comprising a plastically deformable body portion, a tang for deforming the body, and a neck connecting the tang to the body, wherein the neck is designed to break upon application of a predetermined tensile force to the tang, and the body being designed to deform upon application to the tang of less than said predetermined tensile force.

In a further aspect, the invention is directed to a tool for applying the subject clip. In its broadest sense, the tool includes means for gripping and applying tension to the tang, and means for simultaneously pushing against shoulders on the clip body. The tool enables the surgeon to perform the subject method by using the tool first to manipulate the clip into position over opposed tissues. Then, by squeezing or otherwise manipulating the tool, he deforms the clip so as to capture the tissues between the clip's arms and thereby hold the tissues permanently together.

BRIEF DESCRIPTION OF THE DRAWINGS

The invention is illustrated by the following description of a preferred embodiment and by the drawings, wherein:

FIG. 2 is an oblique view of the inventive clip in its original, undeformed condition;

FIG. 3 is a view similar to FIG. 2 showing the clip in a partially deformed condition;

FIG. 4 shows the clip in its fully deformed condition;

FIG. 5 is an elevational view of the inventive clip applier;

FIG. 7 is a view similar to FIG. 1, illustrating the inventive procedure.

DESCRIPTION OF THE PREFERRED EMBODIMENT

Figure 1:
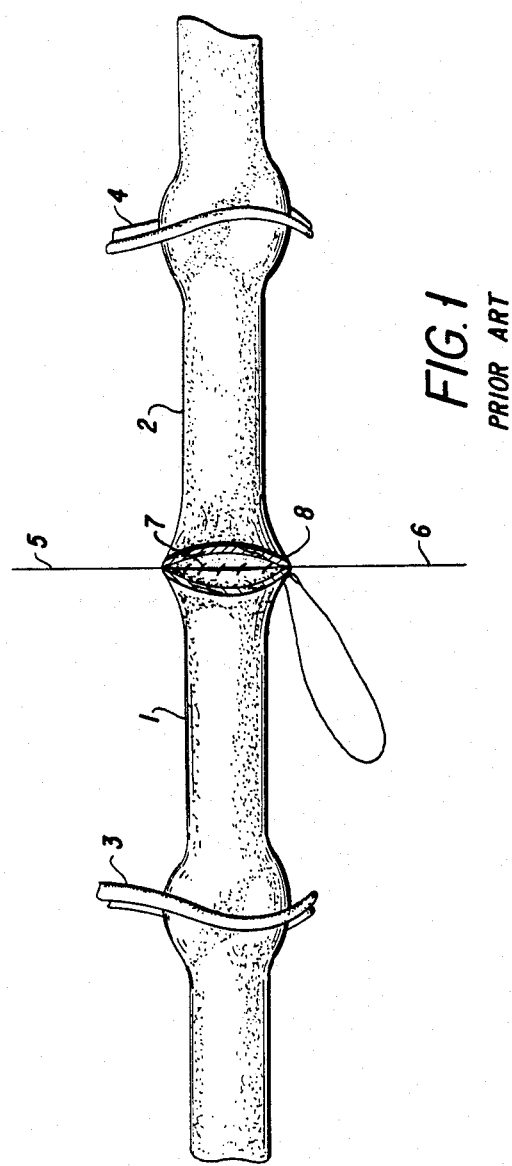
FIG. 1 illustrates a prior art suturing method described above.

As shown in FIG. 2, a surgical clip embodying the invention is formed of a unitary piece of biologically acceptable, plastically deformable material such as a noble metal (i.e. gold, silver, platinum, etc.). While metal clips are presently preferred, it is contemplated that the other materials such as suitable polymer plastics may be used. Whatever the material, it must be sufficiently ductile or plastically deformable so that when the clip is crimped there is minimal spring-back. Otherwise, possible injurious overcrimping, to compensate for the spring-back, would be required.

Structurally, the clip includes a pair of inwardly curved arms 10 and 11 interconnected by a bridging section 12, the two arms extending generally parallel in one direction from the bridging section. The arms terminate at tips 15 and 16 which are rounded to prevent injury to the subject tissue in accordance with an object of this invention. The bridge portion 12 includes a pair of shoulders 17, 18 for engaging the applier tool described below. The center of the bridge is integrally connected to a tang 19 preferably having an enlarged head 20. The connection point is a neck 21 of reduced cross-section designed to break when a predetermined tension is applied to the tang by the tool. The size of the neck is such that its breaking strength ("predetermined tensile force" in the claims below) is greater than the tension required to deform, by bending, the bridge portion of the clip.

The size of the clip will naturally vary according to the application, and we do not intend to limit the scope of this invention to any particular size clip. However, merely as an example, for the anastomosis of a 1-mm vessel, an appropriate size clip has an overall height on the order of 0.030 inches and an overall thickness on the order of 0.006 inches. For this size clip, the radius of curvature of the tip of each arm is approximately 0.0005 inches.

To deform the clip, tension is applied to the tang 19 by a tool such as that described below, while the shoulders are supported by stationary jaw faces on the tool (FIG. 2). The relationship of the jaw faces and the clip shoulders is preferably such that the points of engagement are substantially spaced; i.e., such points are initially remote from the neck. Because of this geometry, application of a tension T to the tang produces a bending moment $M=TX/2$ at the center of the bridge, where X equals the distance from the tang axis to either contact point, as shown in FIG. 3. The neck is sufficiently strong that a bending moment large enough to deform the bridge portion can be produced (FIG. 3). In designing the applier and the clip, the abutting surfaces of the clip shoulders and the jaw faces are so designed that once a desired degree of bending deformation has occurred, the contact points move much closer to the neck, whereafter even substantially increased tang tension does not generate a bending moment sufficient to cause bridge deformation, but rather ultimately fractures the neck 21 (FIG. 4). A particular advantage of this feature is that the amount of bridge deformation is accurately determined by the clip/tool geometry, and is thus independent of the surgeon's manipulating force. As a result, the deformation from clip to clip and from surgeon to surgeon is highly reproducible for a given clip/tool combination. Furthermore, one of skill in the art will appreciate how simple changes in jaw face geometry or clip shoulder shape could be made to produce desired changes in the degree of clip deformation.

Figure 6:
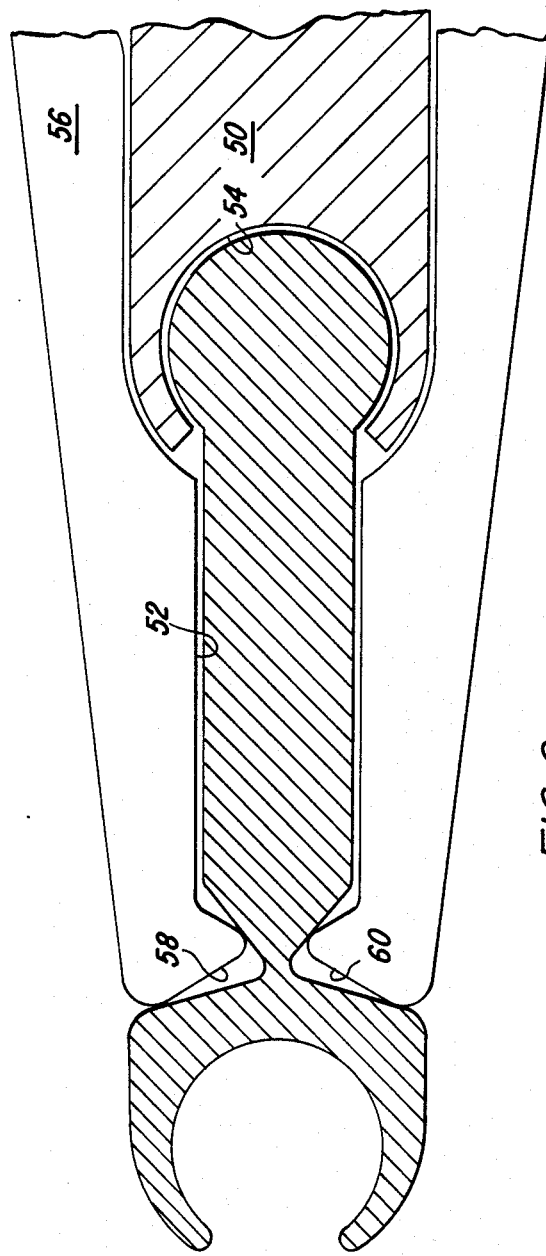
FIG. 6 is an enlarged view of a portion of FIG. 5.

FIGS. 5 and 6 show a clip applier constructed in accordance with this invention. The applier includes means for gripping a clip tang, preferably in the form of a single movable jaw 50 having a slot 52 sized to receive the tang, which slot has an enlarged pocket or recess 54 sized to receive the tang's head. The jaw is supported in a body 56 that terminates at a forward end defined by stationary jaw faces 58, 60 astride the slot and designed to engage the shoulders 17, 18 on the clip. In the embodiment shown, the jaw faces 58, 60 are planar and have between them an obtuse angle A of approximately 120°, which is less than the angle B of approximately 150° between the clip shoulders. Comparing FIGS. 3 and 4, one will note the inward shift in contact point location which results from this geometry as the clip deforms.

The jaw is retracted away from the abutment faces by any of several mechanisms, most preferably a cam-actuated device responsive to squeezing pressure from the surgeon's hand. In this embodiment, shown in FIG. 5, the applier body 56 includes a pair of flexible leaves 62, 64 interconnected at both ends and movable toward each other when the tool is squeezed by the surgeon. Each leaf has an inner surface from which a cam 66 protrudes, the cam having an actuating surface 68 oblique to its direction of movement. As viewed in FIG. 5, the cams are symmetrical in profile, and overlap so as jointly to engage a common cam follower 70. This follower is connected to the jaw 50 as shown. When the leaves are squeezed together, the cam surfaces approach one another, causing the movable jaw 50 to retreat with respect to the stationary jaw faces 58, 60. When a clip is in place within the tool, this action causes deformation as previously described. In FIG. 5, the arcuate shape of the cam faces 68 is noteworthy. This shape makes the ratio of squeezing forces to retracting force an increasing function, giving better feel in situations where it is desired intentionally to limit clip deformation to less than that dictated by the shapes of the abutting surfaces.

While the retracting mechanism is preferably purely mechanical for reasons of simplicity, other mechanisms, such as a fluid-driven piston, or an electrically actuated solenoid, are also contemplated. In any event, what is required is a safe, reliable mechanism for retracting the jaw with respect to the body, responsive to a simple manipulation by the surgeon.

It will be appreciated that the proper geometry for the clip depends on the shape of the applier's jaw and abutment surfaces, and vice-versa. Therefore, these two items must be cooperatively designed.

FIG. 7 illustrates an end-to-end microvascular anastomosis employing the clip and applier described above. In this procedure, a pair of tissues to be joined are first drawn together in apposition (approximated) by suitable means. The edges of the tissues should be partially everted, that is, pursed or flanged outwardly approximately 90° from the axial direction, so that a clip can be placed over the tissue edges, with the arms of the clip astride the point of apposition. Care must be taken not to allow the vessel to cuff back over on itself, since the joint ultimately produced would be weaker than the flanged configuration. Once the clip has been positioned properly with respect to the subject tissues, crimping is effected simply by squeezing together the leaves of the tool. This causes permanent deformation of the microclip bridge section 12, whereafter the clip arms 10, 11 retain the tissues is apposition without puncturing them. This procedure is repeated at as many points as are needed to join the subject tissues securely. The clips, being biologically inert, ordinarily may be left in place permanently. However, in the event that the clip must be removed, a suitable tool may be used to spread the arms 10 and 11.

The clip and applier tool described above provide a sutureless means for the apposition of tissue which is substantially faster than conventional suturing methods, particularly in microvascular anastomosis and which avoids the clotting problem caused by needle perforations. In testing on femoral arteries in rats, short and long term patency and remarkably little damage to the vascular endothelium have been observed.

An advantage of the inventive clips over sutures is the predictability of results. In contrast to hand-made micro-suturing needles, the mass-produced microclips are uniform, producing more uniform results.

An additional advantage is that the speed of application reduces the time blood supply is interrupted, enhancing prospects for vessel patency.

Another advantage is that on any tissues joined in accordance with this invention, the clips are physically independent of one another. Thus, although they securely hold the tissues together at individual points, the clips can move with respect to one another. As a result, their spacing can increase as tissues grow. This makes the present invention particularly attractive for performing anastomoses in children, whose vessels must later expand. Permanent sutures (FIG. 1) must of course be removed if they are not to interfere with vessel growth.

It should be understood that the foregoing description and drawings describe and illustrate but one embodiment of the invention, whose scope should be measured by the following claims.

We claim

1. The combination of:
   (a) a surgical slip comprising
      a plastically deformable bridge portion,
      a pair of spaced arms extending generally parallel in one direction from opposite ends of said bridge,
      a tang extending from said bridge in a direction opposite that of said arms, for deforming said bridge so as to bring said arms together around apposed tissues,
      a neck connecting said tang to said bridge,
      said neck being breakable upon application of a predetermined tensile force to said tang,
      said bridge being deformable by application to the tang of less than said predetermined tensile force, and
      a pair of shoulders on said bridge portion, one on either side of said neck, said shoulders being defined by bearing surfaces having an obtuse angle B between them; and
   (b) a tool for deforming said clip, comprising
      means for gripping and applying tension to said tang, and
      a pair of spaced stationary jaw faces adapted to engage said clip shoulders respectively, wherein said jaw faces are generally flat, and lie at an obtuse angle A with respect to one another, wherein said angles initially are defined by the relationships $120° \leq A < 180°$
   $B \leq 180°$, and
   $A < B$, whereby said jaws initially engage said shoulders at contact points sufficiently widely spaced that the forces developed thereat in reaction to application to said tang of less than said predetermined tensile force cause plastic deformation of said bridge and consequent closure of said arms, and whereby, once the obtuse angle between the shoulders becomes equal to the angle between the jaws, the contact points between the jaws and the arms move closer to one another, whereafter increasing tang tension does not further deform the bridge, but instead results in breakage of said neck.

2. The invention of claim 1, wherein angle B is about 20° greater than angle A.

3. A tool for deforming a surgical clip of the type having a deformable body with a tang extending therefrom and spaced shoulders on the body, one on either side of the tang, said tool comprising
   a tool body,
   a pair of spaced stationary jaws at one end of said body, said jaws having faces adapted to engage said clip shoulders,
   a third jaw movable with respect to said stationary jaws, said third jaw being adapted to grip said clip tang, and
   means for retracting said movable jaw, said means comprising at least one cam in contact with a can follower that is mechanically connected to said movable jaw, and manipulable means connected to said cam, whereby said movable jaw may be retracted by manually displacing said manipulable means.

4. The invention of claim 3, wherein said jaw faces are generally flat, and lie at an obtuse angle in the range of 120° to 180° with respect to one another.

5. The invention of claim 4, wherein said obtuse angle is about 150°.

6. The invention of claim 3, wherein said manipulable means comprises at least one flexible leaf affixed to said body, a portion of said leaf being deflectable by finger pressure with respect to said body, said cam being mounted on said movable portion.

7. The invention of claim 6, comprising two of said leaves, each being integrally connected, at both its ends, to said body whereby the central portions of the leaves can be moved toward one another by squeezing the applier.

8. The invention of claim 3, wherein said claim includes an actuating surface lying oblique to the axis of movement of said movable jaw, and said follower is engaged by said actuating surface.

9. The invention of claim 8, wherein said actuating surface is arcuate.

10. The invention of claim 8, wherein said follower is a roller.

* * * * *